(12) United States Patent
Kahn et al.

(10) Patent No.: US 12,343,137 B1
(45) Date of Patent: *Jul. 1, 2025

(54) HARDWARE SENSOR SYSTEM FOR CONTROLLING SLEEP ENVIRONMENT

(71) Applicant: DP Technologies, Inc., Scotts Valley, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Mihai Ionescu, Ben Lomond, CA (US); Sean Brooks Harre, Santa Cruz, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/492,678

(22) Filed: Oct. 23, 2023

Related U.S. Application Data

(63) Continuation of application No. 16/601,565, filed on Oct. 14, 2019, now Pat. No. 11,793,455.

(Continued)

(51) Int. Cl.
*A61B 5/00* (2006.01)
*A47C 20/00* (2006.01)
(Continued)

(52) U.S. Cl.
CPC ............ *A61B 5/1126* (2013.01); *A47C 20/04* (2013.01); *A47C 20/041* (2013.01);
(Continued)

(58) Field of Classification Search
CPC ... A61B 5/1126; A61B 5/0205; A61B 5/1118; A61B 5/4809; A61B 5/4812;
(Continued)

(56) References Cited

U.S. PATENT DOCUMENTS

| 2,082,843 A | 6/1937 | Mathez |
| 3,541,781 A | 11/1970 | Bloom |

(Continued)

FOREIGN PATENT DOCUMENTS

| AU | 2003203967 A1 | 11/2004 |
| CH | 377738 A | 1/1964 |

(Continued)

OTHER PUBLICATIONS

Choudhary, S. and Choudhary, S, Sleep Effects on Breathing and Respiratory Diseases, Review Article, Oct.-Dec. 2009, 117-122 pages, vol. 26, Issue 4, Department of Pulmonary Medicine, Sleep Medicine, Critical Care, Shree Ramjevan Choudhary Memorial Hospital and Research Centre, Nagpur—02, India, 6 pages.

(Continued)

*Primary Examiner* — Christopher M Brandt
(74) *Attorney, Agent, or Firm* — Nicholson De Vos Webster & Elliott LLP; Judith Szepesi

(57) ABSTRACT

A sleep sensor system comprising a sensor to collect movement data from a sleeper on an adjustable bed, a receiver to send movement data from the sensor to a server. The sleep sensor system further comprising the receiver to receive command data from the server, a bed controller to transmit bed movement command data to the adjustable bed, to cause the adjustable bed to alter one or more settings.

20 Claims, 8 Drawing Sheets

Related U.S. Application Data

(60) Provisional application No. 62/745,976, filed on Oct. 15, 2018, provisional application No. 62/745,978, filed on Oct. 15, 2018, provisional application No. 62/745,984, filed on Oct. 15, 2018.

(51) Int. Cl.
*A47C 20/04* (2006.01)
*A47C 27/08* (2006.01)
*A61B 5/0205* (2006.01)
*A61B 5/11* (2006.01)
*A61G 7/018* (2006.01)
*A61G 7/05* (2006.01)

(52) U.S. Cl.
CPC .......... *A47C 27/083* (2013.01); *A61B 5/0205* (2013.01); *A61B 5/1118* (2013.01); *A61B 5/4809* (2013.01); *A61B 5/4812* (2013.01); *A61B 5/4815* (2013.01); *A61B 5/7264* (2013.01); *A61G 7/018* (2013.01); *A61G 7/05* (2013.01)

(58) Field of Classification Search
CPC ..... A61B 5/4815; A61B 5/7264; A47C 20/04; A47C 20/041; A47C 27/083; A61G 7/018; A61G 7/05
See application file for complete search history.

(56) References Cited

U.S. PATENT DOCUMENTS

| | | | |
|---|---|---|---|
| 3,683,933 A | 8/1972 | Mansfield | |
| 3,798,889 A | 3/1974 | Chadwick | |
| 4,228,806 A | 10/1980 | Lidow | |
| 4,297,685 A | 10/1981 | Brainard, II | |
| 4,322,609 A | 3/1982 | Kato | |
| 4,573,804 A | 3/1986 | Kavoussi et al. | |
| 4,788,533 A | 11/1988 | Mequignon | |
| 4,848,360 A | 7/1989 | Palsgard et al. | |
| 4,858,609 A | 8/1989 | Cole | |
| 4,982,738 A | 1/1991 | Griebel | |
| 5,008,865 A | 4/1991 | Shaffer et al. | |
| 5,047,930 A | 9/1991 | Martens et al. | |
| 5,168,759 A | 12/1992 | Bowman | |
| 5,275,159 A | 1/1994 | Griebel | |
| 5,335,657 A | 8/1994 | Terry et al. | |
| 5,458,105 A | 10/1995 | Taylor et al. | |
| 5,545,192 A | 8/1996 | Czeisler et al. | |
| 5,562,106 A | 10/1996 | Heeke et al. | |
| 5,671,733 A | 9/1997 | Raviv et al. | |
| 5,844,996 A | 12/1998 | Enzmann et al. | |
| 5,868,647 A | 2/1999 | Belsole | |
| 5,928,133 A | 7/1999 | Halyak | |
| 5,961,447 A | 10/1999 | Raviv et al. | |
| 6,014,682 A | 1/2000 | Stephen et al. | |
| 6,045,514 A | 4/2000 | Raviv et al. | |
| 6,231,527 B1 | 5/2001 | Sol | |
| 6,239,706 B1 | 5/2001 | Yoshiike et al. | |
| 6,350,275 B1 | 2/2002 | Vreman et al. | |
| 6,361,508 B1 | 3/2002 | Johnson et al. | |
| 6,468,234 B1 | 10/2002 | Van et al. | |
| 6,547,728 B1 | 4/2003 | Cornuejols | |
| 6,556,222 B1 | 4/2003 | Narayanaswami | |
| 6,834,436 B2 | 12/2004 | Townsend et al. | |
| 6,888,779 B2 | 5/2005 | Mollicone et al. | |
| 6,928,031 B1 | 8/2005 | Kanevsky et al. | |
| 6,963,271 B1 | 11/2005 | Fyffe | |
| 7,006,650 B1 | 2/2006 | Wild | |
| 7,041,049 B1 | 5/2006 | Raniere | |
| 7,106,662 B1 | 9/2006 | Acker, Jr. | |
| 7,139,342 B1 | 11/2006 | Phanse | |
| 7,153,278 B2 | 12/2006 | Ono et al. | |
| 7,280,439 B1 | 10/2007 | Shaddox | |
| 7,366,572 B2 | 4/2008 | Heruth et al. | |
| 7,513,003 B2 | 4/2009 | Mossbeck | |
| 7,559,903 B2 | 7/2009 | Moussavi et al. | |
| 7,572,225 B2 | 8/2009 | Stahmann et al. | |
| 7,652,581 B2 | 1/2010 | Gentry et al. | |
| 7,841,987 B2 | 11/2010 | Sotos et al. | |
| 7,862,226 B2 | 1/2011 | Bracher et al. | |
| 7,868,757 B2 * | 1/2011 | Radivojevic | A61B 5/002 340/575 |
| 7,914,468 B2 | 3/2011 | Shalon et al. | |
| 7,974,849 B1 | 7/2011 | Begole et al. | |
| 8,179,270 B2 | 5/2012 | Rai et al. | |
| 8,193,941 B2 | 6/2012 | Wolfe et al. | |
| 8,398,546 B2 | 3/2013 | Pacione et al. | |
| 8,407,835 B1 | 4/2013 | Connor | |
| 8,475,339 B2 | 7/2013 | Hwang et al. | |
| 8,482,418 B1 | 7/2013 | Harman | |
| 8,577,448 B2 | 11/2013 | Bauer et al. | |
| 8,680,974 B2 | 3/2014 | Meiertoberens et al. | |
| 8,738,925 B1 | 5/2014 | Park et al. | |
| 8,892,036 B1 | 11/2014 | Causey et al. | |
| 8,909,357 B2 * | 12/2014 | Rawls-Meehan | A47C 21/003 700/275 |
| 8,942,719 B1 | 1/2015 | Hyde et al. | |
| 9,060,735 B2 | 6/2015 | Yang et al. | |
| 9,161,719 B2 | 10/2015 | Tsutsumi et al. | |
| 9,257,029 B1 | 2/2016 | Hendrick et al. | |
| 9,448,536 B1 | 9/2016 | Kahn et al. | |
| 9,474,876 B1 | 10/2016 | Kahn et al. | |
| 9,594,354 B1 | 3/2017 | Kahn et al. | |
| 9,675,268 B2 | 6/2017 | Bauer et al. | |
| 9,844,336 B2 | 12/2017 | Zigel et al. | |
| 10,004,452 B2 | 6/2018 | Kazem-Moussavi et al. | |
| 10,207,075 B1 | 2/2019 | Kahn et al. | |
| 10,252,058 B1 | 4/2019 | Fuerst | |
| 10,335,060 B1 | 7/2019 | Kahn et al. | |
| 10,842,968 B1 | 11/2020 | Kahn et al. | |
| 11,100,922 B1 * | 8/2021 | Mutagi | G06F 3/167 |
| 2001/0049482 A1 | 12/2001 | Pozos et al. | |
| 2002/0080035 A1 | 6/2002 | Youdenko | |
| 2002/0100477 A1 | 8/2002 | Sullivan et al. | |
| 2002/0124848 A1 | 9/2002 | Sullivan et al. | |
| 2003/0095476 A1 | 5/2003 | Mollicone et al. | |
| 2003/0204412 A1 | 10/2003 | Brier | |
| 2003/0204909 A1 | 11/2003 | Lane | |
| 2003/0227439 A1 | 12/2003 | Lee et al. | |
| 2003/0231495 A1 | 12/2003 | Lee | |
| 2004/0034289 A1 | 2/2004 | Teller et al. | |
| 2004/0049132 A1 | 3/2004 | Barron et al. | |
| 2004/0071382 A1 | 4/2004 | Rich et al. | |
| 2004/0111039 A1 | 6/2004 | Minamiura et al. | |
| 2004/0133081 A1 | 7/2004 | Teller et al. | |
| 2004/0210155 A1 | 10/2004 | Takemura et al. | |
| 2004/0218472 A1 | 11/2004 | Narayanaswami et al. | |
| 2005/0012622 A1 | 1/2005 | Sutton | |
| 2005/0043645 A1 | 2/2005 | Ono et al. | |
| 2005/0075116 A1 | 4/2005 | Laird et al. | |
| 2005/0076715 A1 | 4/2005 | Kuklis et al. | |
| 2005/0143617 A1 | 6/2005 | Auphan | |
| 2005/0154330 A1 | 7/2005 | Loree et al. | |
| 2005/0190065 A1 | 9/2005 | Ronnholm | |
| 2005/0236003 A1 | 10/2005 | Meader | |
| 2005/0237479 A1 | 10/2005 | Rose | |
| 2005/0245793 A1 | 11/2005 | Hilton et al. | |
| 2005/0283039 A1 | 12/2005 | Cornel | |
| 2005/0288904 A1 | 12/2005 | Warrior et al. | |
| 2006/0017560 A1 | 1/2006 | Albert | |
| 2006/0025299 A1 | 2/2006 | Miller et al. | |
| 2006/0064037 A1 | 3/2006 | Shalon et al. | |
| 2006/0097884 A1 | 5/2006 | Jang et al. | |
| 2006/0136018 A1 | 6/2006 | Lack et al. | |
| 2006/0150734 A1 | 7/2006 | Mimnagh-Kelleher et al. | |
| 2006/0252999 A1 | 11/2006 | Devaul et al. | |
| 2006/0266356 A1 | 11/2006 | Sotos et al. | |
| 2006/0279428 A1 | 12/2006 | Sato et al. | |
| 2006/0293602 A1 | 12/2006 | Clark | |
| 2006/0293608 A1 | 12/2006 | Rothman et al. | |
| 2007/0016091 A1 | 1/2007 | Butt et al. | |
| 2007/0016095 A1 | 1/2007 | Low et al. | |
| 2007/0093722 A1 | 4/2007 | Noda et al. | |

(56) References Cited

U.S. PATENT DOCUMENTS

| | | |
|---|---|---|
| 2007/0100666 A1 | 5/2007 | Stivoric et al. |
| 2007/0129644 A1 | 6/2007 | Richards et al. |
| 2007/0139362 A1 | 6/2007 | Colton et al. |
| 2007/0191692 A1 | 8/2007 | Hsu et al. |
| 2007/0239225 A1 | 10/2007 | Saringer |
| 2007/0250286 A1 | 10/2007 | Duncan et al. |
| 2007/0251997 A1 | 11/2007 | Brown et al. |
| 2007/0287930 A1 | 12/2007 | Sutton |
| 2008/0062818 A1 | 3/2008 | Plancon et al. |
| 2008/0109965 A1 | 5/2008 | Mossbeck |
| 2008/0125820 A1 | 5/2008 | Stahmann et al. |
| 2008/0169931 A1 | 7/2008 | Gentry et al. |
| 2008/0191885 A1 | 8/2008 | Loree et al. |
| 2008/0234785 A1 | 9/2008 | Nakayama et al. |
| 2008/0243014 A1 | 10/2008 | Moussavi et al. |
| 2008/0269625 A1 | 10/2008 | Halperin et al. |
| 2008/0275348 A1 | 11/2008 | Catt et al. |
| 2008/0275349 A1 | 11/2008 | Halperin et al. |
| 2008/0289637 A1 | 11/2008 | Wyss |
| 2008/0319277 A1 | 12/2008 | Bradley |
| 2009/0030767 A1 | 1/2009 | Morris et al. |
| 2009/0048540 A1 | 2/2009 | Otto et al. |
| 2009/0069644 A1 | 3/2009 | Hsu et al. |
| 2009/0071810 A1 | 3/2009 | Hanson et al. |
| 2009/0082699 A1 | 3/2009 | Bang et al. |
| 2009/0094750 A1 | 4/2009 | Oguma et al. |
| 2009/0105785 A1 | 4/2009 | Wei et al. |
| 2009/0121826 A1 | 5/2009 | Song et al. |
| 2009/0128487 A1 | 5/2009 | Langereis et al. |
| 2009/0143636 A1 | 6/2009 | Mullen et al. |
| 2009/0150217 A1 | 6/2009 | Luff |
| 2009/0177327 A1 | 7/2009 | Turner et al. |
| 2009/0203970 A1 | 8/2009 | Fukushima et al. |
| 2009/0203972 A1 | 8/2009 | Heneghan et al. |
| 2009/0207028 A1 | 8/2009 | Kubey et al. |
| 2009/0209839 A1 | 8/2009 | Ochs et al. |
| 2009/0227888 A1 | 9/2009 | Salmi et al. |
| 2009/0264789 A1 | 10/2009 | Molnar et al. |
| 2009/0320123 A1 | 12/2009 | Yu et al. |
| 2010/0010330 A1 | 1/2010 | Rankers et al. |
| 2010/0010565 A1 | 1/2010 | Lichtenstein et al. |
| 2010/0036211 A1 | 2/2010 | La et al. |
| 2010/0061596 A1 | 3/2010 | Mostafavi et al. |
| 2010/0075807 A1 | 3/2010 | Hwang et al. |
| 2010/0079291 A1 | 4/2010 | Kroll et al. |
| 2010/0079294 A1 | 4/2010 | Rai et al. |
| 2010/0083968 A1 | 4/2010 | Wondka et al. |
| 2010/0094139 A1 | 4/2010 | Brauers et al. |
| 2010/0094148 A1 | 4/2010 | Bauer et al. |
| 2010/0100004 A1 | 4/2010 | Van Someren |
| 2010/0102971 A1 | 4/2010 | Mrtanen et al. |
| 2010/0152543 A1 | 6/2010 | Heneghan et al. |
| 2010/0152546 A1 | 6/2010 | Behan et al. |
| 2010/0217146 A1 | 8/2010 | Osvath |
| 2010/0256512 A1 | 10/2010 | Sullivan |
| 2010/0277316 A1 | 11/2010 | Schlangen et al. |
| 2010/0283618 A1 | 11/2010 | Wolfe et al. |
| 2010/0331145 A1 | 12/2010 | Lakovic et al. |
| 2011/0015467 A1 | 1/2011 | Dothie et al. |
| 2011/0015495 A1 | 1/2011 | Dothie et al. |
| 2011/0018720 A1 | 1/2011 | Rai et al. |
| 2011/0046498 A1 | 2/2011 | Klap et al. |
| 2011/0054279 A1 | 3/2011 | Reisfeld et al. |
| 2011/0058456 A1 | 3/2011 | Van et al. |
| 2011/0087076 A1 | 4/2011 | Brynelsen et al. |
| 2011/0090226 A1 | 4/2011 | Sotos et al. |
| 2011/0105915 A1 | 5/2011 | Bauer et al. |
| 2011/0137836 A1 | 6/2011 | Kuriyama et al. |
| 2011/0160619 A1 | 6/2011 | Gabara |
| 2011/0190594 A1 | 8/2011 | Heit et al. |
| 2011/0199218 A1 | 8/2011 | Caldwell et al. |
| 2011/0224510 A1 | 9/2011 | Oakhill |
| 2011/0230790 A1 | 9/2011 | Kozlov |
| 2011/0245633 A1 | 10/2011 | Goldberg et al. |
| 2011/0295083 A1 | 12/2011 | Doelling et al. |
| 2011/0302720 A1 | 12/2011 | Yakam et al. |
| 2011/0304240 A1 | 12/2011 | Meitav et al. |
| 2012/0004749 A1 | 1/2012 | Abeyratne et al. |
| 2012/0083715 A1 | 4/2012 | Yuen et al. |
| 2012/0232414 A1 | 9/2012 | Mollicone et al. |
| 2012/0243379 A1 | 9/2012 | Balli |
| 2012/0253220 A1 | 10/2012 | Rai et al. |
| 2012/0286954 A1 | 11/2012 | Cullen |
| 2012/0296156 A1 | 11/2012 | Auphan |
| 2013/0012836 A1 | 1/2013 | Crespo et al. |
| 2013/0018284 A1 | 1/2013 | Kahn et al. |
| 2013/0023214 A1 | 1/2013 | Wang et al. |
| 2013/0053653 A1 | 2/2013 | Cuddihy et al. |
| 2013/0053656 A1 | 2/2013 | Mollicone et al. |
| 2013/0060306 A1 | 3/2013 | Colbauch |
| 2013/0144190 A1 | 6/2013 | Bruce et al. |
| 2013/0162423 A1 | 6/2013 | Rowe et al. |
| 2013/0184601 A1 | 7/2013 | Zigel et al. |
| 2013/0197857 A1 | 8/2013 | Lu et al. |
| 2013/0204314 A1 | 8/2013 | Miller et al. |
| 2013/0208576 A1 | 8/2013 | Loree et al. |
| 2013/0278429 A1 | 10/2013 | Sakai |
| 2013/0283530 A1 | 10/2013 | Main et al. |
| 2013/0286793 A1 | 10/2013 | Umamoto |
| 2013/0289419 A1 | 10/2013 | Berezhnyy et al. |
| 2013/0300204 A1 * | 11/2013 | Partovi .................. B60L 58/15 |
| | | 307/104 |
| 2013/0310658 A1 | 11/2013 | Ricks et al. |
| 2013/0344465 A1 | 12/2013 | Dickinson et al. |
| 2014/0005502 A1 | 1/2014 | Klap et al. |
| 2014/0051938 A1 | 2/2014 | Goldstein et al. |
| 2014/0085077 A1 | 3/2014 | Luna et al. |
| 2014/0135955 A1 | 5/2014 | Burroughs |
| 2014/0171815 A1 | 6/2014 | Yang et al. |
| 2014/0200691 A1 | 7/2014 | Lee et al. |
| 2014/0207292 A1 | 7/2014 | Ramagem et al. |
| 2014/0218187 A1 | 8/2014 | Chun et al. |
| 2014/0219064 A1 | 8/2014 | Filipi et al. |
| 2014/0232558 A1 | 8/2014 | Park et al. |
| 2014/0256227 A1 | 9/2014 | Aoki et al. |
| 2014/0259417 A1 * | 9/2014 | Nunn ..................... A47C 21/04 |
| | | 5/713 |
| 2014/0259434 A1 | 9/2014 | Nunn et al. |
| 2014/0273858 A1 | 9/2014 | Panther et al. |
| 2014/0276227 A1 | 9/2014 | Barroeta |
| 2014/0288878 A1 | 9/2014 | Donaldson |
| 2014/0306833 A1 | 10/2014 | Ricci |
| 2014/0350351 A1 | 11/2014 | Halperin et al. |
| 2014/0371635 A1 | 12/2014 | Shinar et al. |
| 2015/0015399 A1 | 1/2015 | Gleckler et al. |
| 2015/0068069 A1 | 3/2015 | Tran et al. |
| 2015/0073283 A1 | 3/2015 | Van et al. |
| 2015/0085622 A1 | 3/2015 | Carreel et al. |
| 2015/0094544 A1 | 4/2015 | Spolin et al. |
| 2015/0094618 A1 | 4/2015 | Russell et al. |
| 2015/0098309 A1 | 4/2015 | Adams et al. |
| 2015/0101870 A1 | 4/2015 | Gough et al. |
| 2015/0136146 A1 | 5/2015 | Hood et al. |
| 2015/0141852 A1 | 5/2015 | Dusanter et al. |
| 2015/0148621 A1 | 5/2015 | Sier |
| 2015/0148871 A1 | 5/2015 | Maxik et al. |
| 2015/0164238 A1 | 6/2015 | Benson et al. |
| 2015/0164409 A1 | 6/2015 | Benson et al. |
| 2015/0164438 A1 | 6/2015 | Halperin et al. |
| 2015/0164682 A1 | 6/2015 | Remmers et al. |
| 2015/0173671 A1 | 6/2015 | Paalasmaa et al. |
| 2015/0178362 A1 | 6/2015 | Wheeler |
| 2015/0190086 A1 | 7/2015 | Chan et al. |
| 2015/0220883 A1 | 8/2015 | Lingg et al. |
| 2015/0233598 A1 | 8/2015 | Shikii et al. |
| 2015/0238139 A1 | 8/2015 | Raskin et al. |
| 2015/0265903 A1 | 9/2015 | Kolen et al. |
| 2015/0289802 A1 | 10/2015 | Thomas et al. |
| 2015/0320588 A1 | 11/2015 | Connor |
| 2015/0333950 A1 | 11/2015 | Johansson |
| 2015/0346824 A1 | 12/2015 | Chen et al. |
| 2015/0351694 A1 | 12/2015 | Shimizu et al. |
| 2016/0015315 A1 | 1/2016 | Auphan et al. |
| 2016/0045035 A1 | 2/2016 | Van Erlach |

(56) References Cited

U.S. PATENT DOCUMENTS

| | | | |
|---|---|---|---|
| 2016/0217672 | A1 | 7/2016 | Yoon et al. |
| 2016/0262693 | A1 | 9/2016 | Sheon |
| 2016/0287869 | A1 | 10/2016 | Errico et al. |
| 2017/0003666 | A1 | 1/2017 | Nunn et al. |
| 2017/0020756 | A1 | 1/2017 | Hillenbrand et al. |
| 2017/0188938 | A1* | 7/2017 | Toh .................. H04W 4/38 |
| 2018/0049701 | A1 | 2/2018 | Raisanen |
| 2018/0103770 | A1 | 4/2018 | Nava et al. |
| 2018/0338725 | A1* | 11/2018 | Shan .................. A61B 5/6892 |
| 2019/0021675 | A1* | 1/2019 | Gehrke .................. A61G 7/015 |
| 2019/0044380 | A1 | 2/2019 | Lausch et al. |
| 2019/0132570 | A1 | 5/2019 | Chen et al. |
| 2019/0156296 | A1* | 5/2019 | Lu .................. A61B 5/024 |
| 2019/0190992 | A1* | 6/2019 | Warrick .................. H04L 67/125 |
| 2019/0201270 | A1* | 7/2019 | Sayadi .................. A61B 5/4836 |

FOREIGN PATENT DOCUMENTS

| | | |
|---|---|---|
| CH | 668349 A | 12/1988 |
| CH | 697528 B1 | 11/2008 |
| DE | 4101471 A1 | 7/1992 |
| DE | 19642316 A1 | 4/1998 |
| EP | 1139187 A2 | 10/2001 |
| JP | 08-160172 A | 6/1996 |
| JP | 2007-132581 A | 5/2007 |
| KR | 10-2008-0096965 A | 11/2008 |
| KR | 10-2009-0085403 A | 8/2009 |
| KR | 10-2010-0022217 A | 3/2010 |
| WO | 93/02731 A1 | 2/1993 |
| WO | 2008/038288 A2 | 4/2008 |
| WO | 2009/099292 A2 | 8/2009 |
| WO | 2011/141840 A1 | 11/2011 |
| WO | 2013/014578 A1 | 1/2013 |

OTHER PUBLICATIONS

Ding, F., et al., "Polysomnographic validation of an under-mattress monitoring device in estimating sleep architecture and obstructive sleep apnea in adults," Sleep Medicine, vol. 96, Apr. 2022, pp. 20-27.

Verbraecken, J, Applications of Evolving Technologies in Sleep Medicine, Article, Dec. 2013, 443-455 pages, vol. 9, No. 6, Dept of Pulmonary Medicine and Multidisciplinary Sleep Disorders Centre, Antwerp University Hospital, Antwerp, Belgium, 14 pages.

"NPL—EasySense LTD", archive.org, accessed: Jan. 7, 2019, published: Nov. 27, 2006.

Acligraphy, From Wikipedia, the free encyclopedia, downloaded at: http://en.wikipedia.org/wiki/Actigraphy on Apr. 24, 2014, 4 pages.

Advisory Action, U.S. Appl. No. 15/071,191, Jan. 27, 2023, 3 pages.

Advisory Action, U.S. Appl. No. 17/647,160, Jan. 10, 2023, 3 pages.

Campbell, Appleinsider, "Apple buys sleep tracking firm Beddit" May 9, 2017. Retrieved from https://appleinsider.com/articles/17/05/09/apple-buys-sleep-tracking-firm-beddit (Year: 2017).

Crist, CNET "Samsung introduces SleepSense" Sep. 3, 2015. Retrieved from https://www.cnet.com/reviews/samsung-sleepsense-preview (Year: 2015).

Daniel et al., "Activity Characterization from Actimetry Sensor Data for Sleep Disorders Diagnosis", Sep. 2008, 10 pages.

Desai, Rajiv, "The Sleep",Mar. 17, 2011, Educational Blog, 82 pages.

Final Office Action, U.S. Appl. No. 15/071,189, Nov. 28, 2022, 22 pages.

Final Office Action, U.S. Appl. No. 16/799,786, Dec. 9, 2022, 16 pages.

Fitbit Product Manual, "Fitbit Product Manual", available online at <http://www.filtbit.com/manual>, Mar. 29, 2010, pp. 1-20.

Haughton Mifflin, "Estimate", The American Heritage dictionary of the English language (5th ed.), Jul. 24, 2017, 2 pages.

How BodyMedia FIT Works, available online at <http://www.bodymedia.com/Shop/Learn-More/How-it-works>, Jun. 17, 2011, 2 pages.

Internet Archive, Withings "Sleep Tracking Mat" Nov. 22, 2018. Retrieved from https://web.archive.org/web/20181122024547/https://www.withings.com/us/en/sleep (Year: 2018).

Jaines, Kira, "Music to Help You Fall Asleep," <http://www.livestrong.com/article/119802-music-fall-sleep/>, May 10, 2010, 2 pages.

Jetlog Reviewers Guide, <http://www.jetlog.com/fileadmin/Presse_us/24x7ReviewersGuide.pdf>, 2009, 5 pages.

Leeds, Joshua, "Sound-Remedies.com: Sonic Solutions for Health, Learning & Productivity," <http://www.sound-remedies.com/ammusforslee.html>, Accessed May 23, 2013, 2 pages.

Lichstein, et al., "Actigraphy Validation with Insomnia", Sleep, vol. 29, No. 2, 2006, pp. 232-239.

Liden et al., "Characterization and Implications of the Sensors Incorporated into the SenseWear(TM) Armband for Energy Expenditure and Activity Detection", 2011, 7 pages.

Mattila et al., "A Concept for Personal Wellness Management Based on Activity Monitoring," Pervasive Computing Technologies for Healthcare, 2008.

Non-Final Office Action, U.S. Appl. No. 16/601,565, Nov. 1, 2022, 15 pages.

Notice of Allowance, U.S. Appl. No. 16/601,565, Feb. 13, 2023, 5 pages.

Patel, et al., Validation of Basis Science Advanced Sleep Analysis, Estimation of Sleep Stages and Sleep Duration, Basis Science, San Francisco, CA, Jan. 2014, 6 pages.

Pollak et al., "How Accurately Does Wrist Actigraphy Identify the States of Sleep and Wakefulness?", Sleep, vol. 24, No. 8, 2001, pp. 957-965.

Power Nap, <en.wikipedia.org/wiki/Power.sub.--nap>, Last Modified Sep. 20, 2012, 4 pages.

PowerNap, "iPhone App", available online at <http://forums.precentral.net/webos-apps-software/223091-my-second-app-powernap-out-app-catalog-nap-timer.html>, Jan. 6, 2010, 10 pages.

Rechtschaffen et al., Manual of Standardized Terminology, Techniques and Scoring System for Sleep Stages of Human Subjects, 1968, 57 pages.

Requirement for Restriction/Election, U.S. Appl. No. 16/601,565, Aug. 15, 2022, 6 pages.

Sara Mednick, <en.wikipedia.org/wiki/Sara.sub.-Mednick>, Last Modified Sep. 12, 2012, 2 pages.

Schulz et al. "Phase shift in the REM sleep rhythm." Pflugers Arch. 358, 1975, 10 pages.

Schulz et al. "The REM-NREM sleep cycle: Renewal Process or Periodically Driven Process?." Sleep, 1980, pp. 319-328.

Slow Wave Sleep, <en.wikipedia.org/wiki/Slow-wave.sub.-sleep>, Last Modified Jul. 22, 2012, 4 pages.

Sunseri et al., "The SenseWear (TM) Armband as a Sleep Detection Device," available online at <http://sensewear.bodymedia.com/SenseWear-Sludies/SW-Whilepapers/The-SenseWear-armband-as-a-Sleep-Delection-Device>, 2005, 9 pages.

Wikipedia , "Sleep", available online at <https://en.wikipedia.org/wiki/Sleep#Physiology>, Oct. 5, 2012, 21 pages.

Wikipedia, "David.sub Dinges", available online at <en.wikipedia.org/wiki/David.sub_Dinges>, Sep. 12, 2012, 2 pages.

Wikipedia, "Sleep Debt", available online at <https://en.wikipedia.org/wiki/Sleep_debt>,Aug. 25, 2012, 3 pages.

Wikipedia, "Sleep Inertia", available online at <en.wikipedia.org/wiki/Sleep_inertia>, Sep. 12, 2012, 2 pages.

Yassourdidis et al. "Modelling and Exploring Human Sleep with Event History Analysis." Journal of Sleep Research, 1999, pp. 25-36.

Gaiduk et al.,"Automatic sleep stages classification using respiratory, heart rate and movement signals", Institute of Physics and Engineering in Medicine, 2018, 14 pages.

Ilhan et al., "Sleep stage classification via ensemble and conventional machine learning methods using single channel EEG signals", Intelligent Systems and Applications in Engineering, Dec. 28, 2017, pp. 174-184.

\* cited by examiner

HARDWARE SENSOR SYSTEM FOR CONTROLLING SLEEP ENVIRONMENT

RELATED APPLICATION

The present application is a continuation of U.S. patent application Ser. No. 16/601,565, filed Oct. 14, 2019, issuing as U.S. Pat. No. 11,793,455 on Oct. 24, 2023, which application claims priority to U.S. Provisional Patent Application No. 62/745,978 filed on Oct. 15, 2018; U.S. Provisional Patent Application No. 62/745,976 (8689P231Z) filed on Oct. 15, 2019; and U.S. Provisional Application No. 62/745,984 (8689P233Z) filed on Oct. 15, 2019. All of the aforementioned applications are incorporated herein by reference in their entirety.

FIELD

The present invention relates to sleep sensors, and more particularly to a sensor system including Internet of Things controls.

BACKGROUND

An average person spends about one-third of his or her life asleep. Sleep is the time our bodies undergo repair and detoxification. Research has shown that poor sleep patterns is an indication of and often directly correlated to poor health. Proper, restful and effective sleep has a profound effect on our mental, emotional and physical well-being.

Every person has a unique circadian rhythm that, without manipulation, will cause the person to consistently go to sleep around a certain time and wake up around a certain time. For most people, a typical night's sleep is comprised of five different sleep cycles, each lasting about 90 minutes. The first four stages of each cycle are often regarded as quiet sleep or non-rapid eye movement (NREM). The final stage is often denoted by and referred to as rapid eye movement (REM). REM sleep is thought to help consolidate memory and emotion. REM sleep is also the time when blood flow rises sharply in several areas of the brain that are linked to processing memories and emotional experiences. During REM sleep, areas of the brain associated with complex reasoning and language experience blood flow declines, whereas areas of the brain associated with processing memories and emotional experiences exhibit increased blood flow.

Therefore, it is useful for everyone to know more about how well they sleep.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

A sleep monitoring system is described. The system includes user-side elements including a sensor element and a receiver. The receiver interfaces with a bed controller, which in one embodiment enables changing the position of the head and/or foot of the bed. In one embodiment, the bed controller also permits changing a temperature, heating/cooling of the bed. In one embodiment, the bed controller also permits alteration of air flow. The receiver system, in one embodiment, also enables interface with external Internet of Things (IoT) elements, enabling a user to control the bed via existing IoT infrastructure, such as AMAZON's Alexa or GOOGLE Home, or APPLE Siri, or other such devices. The receiver system further enables the adjustment of the bed based on sleep analytics. In one embodiment, the receiver interfaces with the bed using a DIN connector, which provides power to the bed, and provides a command interface from the receiver to the bed. In this way, a controlled bed can become a "smart bed" which is part of the IoT infrastructure.

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

Figure 1:
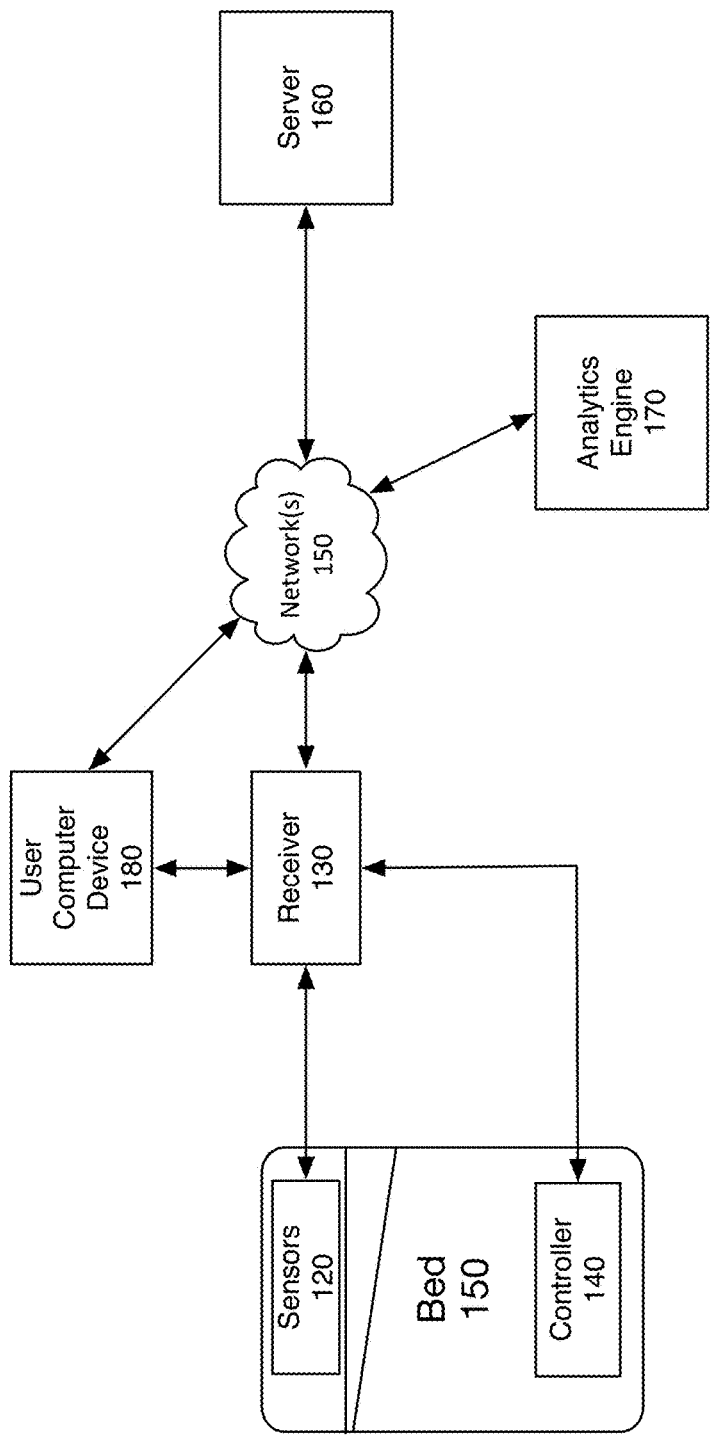
FIG. 1 is block diagram of one embodiment of a system in which the sensor system may be implemented.

FIG. 1 is block diagram of one embodiment of a system in which the sensor system may be implemented. The system includes a sleep analytics system 100 including sensors 120, receiver 130, server 160, and analytics engine 170. In one embodiment, the client portion of the sleep analytics system 100 is located in a user's home and includes the sensors 120 and receiver 130.

In one embodiment, the receiver 130 is coupled to sensors 120 via a cable. In another embodiment the connection may be wireless, such as low power Bluetooth (BLE), Wi-Fi, or another type of wireless connection. In one embodiment, receiver 130 also may be coupled to a controller 140, which controls bed 150. In one embodiment, this connection is a wired connection. Alternatively, it may be a wireless connection.

In one embodiment, the sensors 120 may include one or more sensors positioned in bed 150 which are used to measure the user's sleep. In one embodiment, sensors 120 may include sensors which are not in bed 150 but positioned in the room in which the bed 150 is located. In one embodiment, one or more these additional sensors may be built into receiver 130. In one embodiment, there may be external sensors which may be coupled to receiver 130 either via wires or wirelessly. The receiver 130 collects data from the one or more sensors, for transmission to the server 160.

In one embodiment, the receiver 130 is coupled to the server 160 via a network 150. The server portion includes server 160 and analytics engine 170, which in one embodiment are located off-site, removed from the user. In another embodiment, the server may be a local system, such as a computer system running an application. The network 150 may be the Internet, and the receiver 130 may send data to the server via a wireless network, such as Wi-Fi or the cellular network. In one embodiment, server 160 and analytics engine 170 may be on the same physical device. In one embodiment, server and/or analytics engine 170 may include a plurality of devices. In one embodiment, one or both of the server 160 and the analytics engine 170 may be using cloud computing and may be implemented as a distributed system.

In one embodiment, the user may be provided information about their sleep experience and the ability to set preferences via a computer device 180. In one embodiment, the user computer device 180 may be a mobile telephone, tablet, laptop, or desktop computer running an application or providing access to a website. In one embodiment, the user computer device 180 may be an IoT device such as AMAZON's Alexa or GOOGLE Home, or APPLE Siri. In one embodiment, the user computer device 180 may obtain data from the server 160 and/or analytics engine 170 via the network 150. In one embodiment, the user computer device 180 may connect to the server 160/analytics engine 170 via the receiver 130.

Figure 2A:
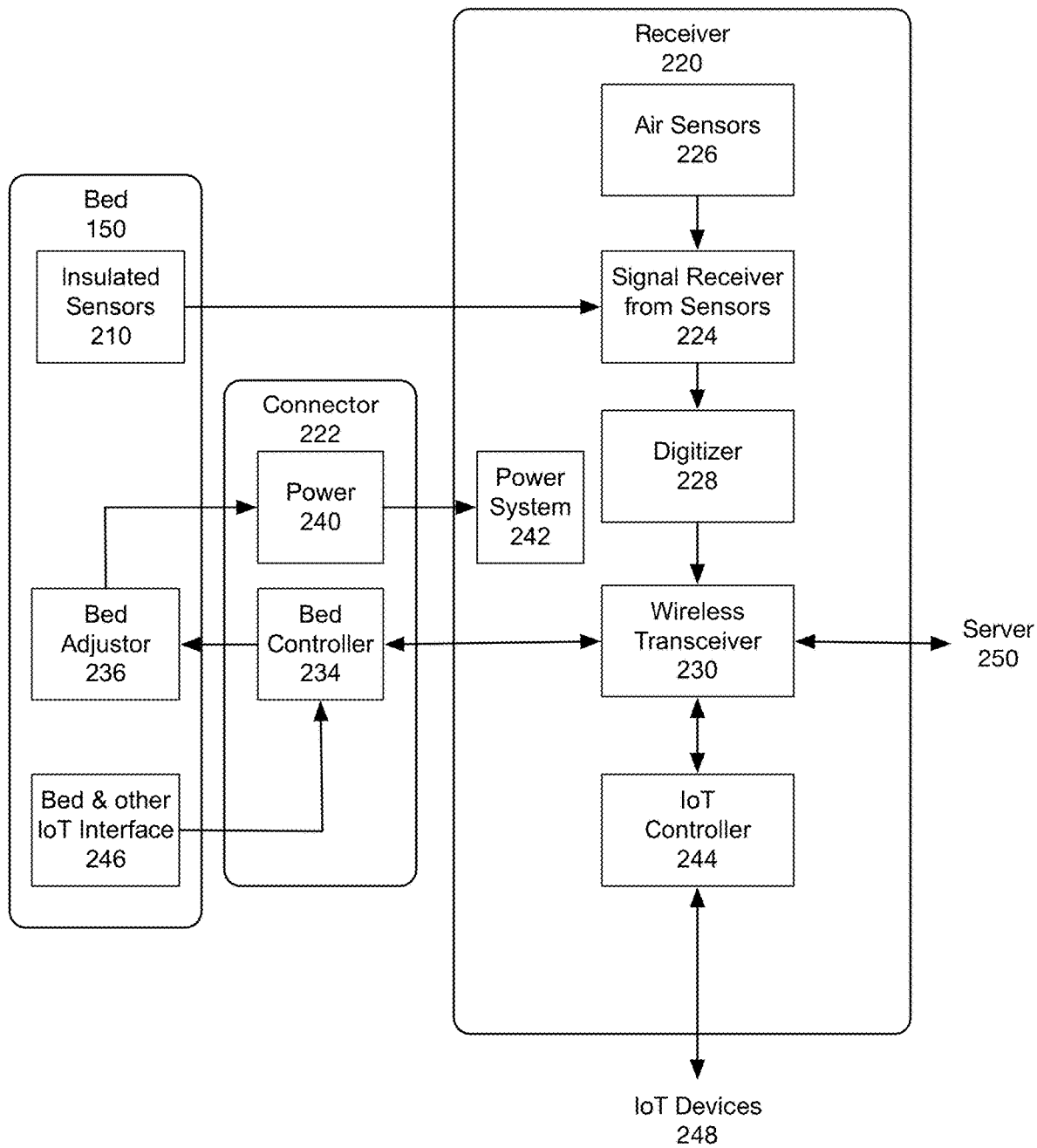
FIG. 2A is a block diagram of one embodiment of the user site portion of the sensor system.

FIG. 2A is a block diagram of one embodiment of the user site portion of the sensor system. The user site portion includes a bed 150 or other sleeping surface. In one embodiment, the bed 150 includes a bed adjustor 236, and optionally an IoT interface 246. The insulated sensors 210 are placed in the bed 150 in one embodiment. The insulated sensors 210 may be built into the bedframe, placed under a mattress or mattress topper, or otherwise positioned such that they are underneath the sleeper. The data from sensors 210 goes to signal receiver 224 in receiver 220. In one embodiment, the receiver 220 may also include one or more additional sensors 226 such as air sensors 226. Air sensors 226, in one embodiment, may include temperature, humidity, and volatile organic compound (VOC) sensors. Other types of environmental sensors may also be included in receiver 220. In one embodiment, additional external sensors may also be coupled to receiver 220 wirelessly or via wired connections.

The signal data is digitized by digitizer 228. In one embodiment, an analog-to-digital converter is used. The data is then sent to server 250 via wireless transceiver 230. The server 250 processes the data, and returns data to the wireless transceiver 230.

The data from the server 250 may be used to adjust the sensors 210, and the receiver 220's functionality. Furthermore, in one embodiment, the data from the server 250 may be used to control IoT devices 248 via IoT controller 244. In one embodiment, the IoT controller 244 may be a connection to an IoT device 248 such as a speaker system, light controls, television controls, or other such devices which may be remotely controlled.

In one embodiment, the data from the server 250 may also be used to control the bed 150. In one embodiment, command data may be transmitted through a connector 222 to the bed adjustor 236 within the bed 150. The bed adjuster 236 controls the bed 150, via one or more motors or other control systems.

In one embodiment, connector 222 provides a physical connection from the receiver 220 to the bed adjustor 236. In one embodiment, the connector 222 also provides power 240 to receiver 220. In one embodiment, the bed adjustor 236 is plugged into wall power. Since the bed adjustor controls setting of a large physical device, the bed 150, it utilizes standard wall power, in one embodiment. In contrast, the systems of the receiver 220 consumes very little power. The receiver 220 may have a single connection through connector 222 to the bed adjustor 236 which provides power, and also provides signal and receives data from receiver 220. In one embodiment, the connection is a DIN plug. In one embodiment, the DIN connector used is a standard connector for audio signals which provides a circular shielding metal skirt protecting a number of straight round pins. This ensures that the plug is inserted with the correct orientation and ensures that the shielding is connected between socket and plug prior to any signal path connection being made. Power system 242 in receiver 220 provides a step-down voltage converter to ensure that the power available to the receiver 220 is appropriate. In one embodiment, the receiver 220 may utilize multiple power elements to step down power from the level provided from the power output 240 of connector 222.

In one embodiment, this system additional provides the ability to interact with the bed 150 via IoT even if the bed itself does not include the optional native IoT interface 246, using the IoT controller 244 in the receiver 220. This may enable a user to for example utilize voice commands through a system such as AMAZON's Alexa, GOOGLE Home, or APPLE Siri to adjust the bed position, instead of utilizing controls associated with the bed.

Furthermore, in one embodiment, the system also allows the receiver 220 to control IoT devices 248 to adjust the user's environment based on the user's sleep state, as determined by server 250. For example, if the user has fallen asleep, the IoT systems 248 may lock the door, close the blinds, adjust the temperature, adjust the bed position, or otherwise adjust the environment to ensure that the user has a restful sleep. Similarly, if an alarm is set, the IoT controller 244 may control IoT devices 248 to transition the user smoothly to a waking state, to maximize comfort and ensure that the user wakes in the correct portion of their sleep cycle to minimize post-sleep tiredness.

In one embodiment, air sensor 226 data may be used by server 250 to adjust the environment and/or provide alerts to the user, if needed. In one embodiment, such alerts may be provided through an application on a computer system such as a mobile phone, an IoT interface, or other device which provides data to the user about their sleep experience and environment. In one embodiment, air sensor data 226 may also be used to automatically adjust the user's environment to ensure healthy air quality. For example, if the air is determined to be too dry, a humidifier may be turned on, via IoT controller 244. If the air has too many VOCs, a window may be opened, a fan may be turned on, etc. In one embodiment, the system determines whether it is possible to address the issue via existing IoT devices. If that is not possible due to a problem which cannot be addressed by the existing IoT devices 248 the user may be alerted. In one embodiment, an alert may ask the user to take a particular corrective step, e.g. open windows, run a humidifier, run an air filter, etc. In one embodiment, the user is informed of changes to their environment via IoT devices 248, but alerts are sent only when the user's action is needed.

Figure 2B:
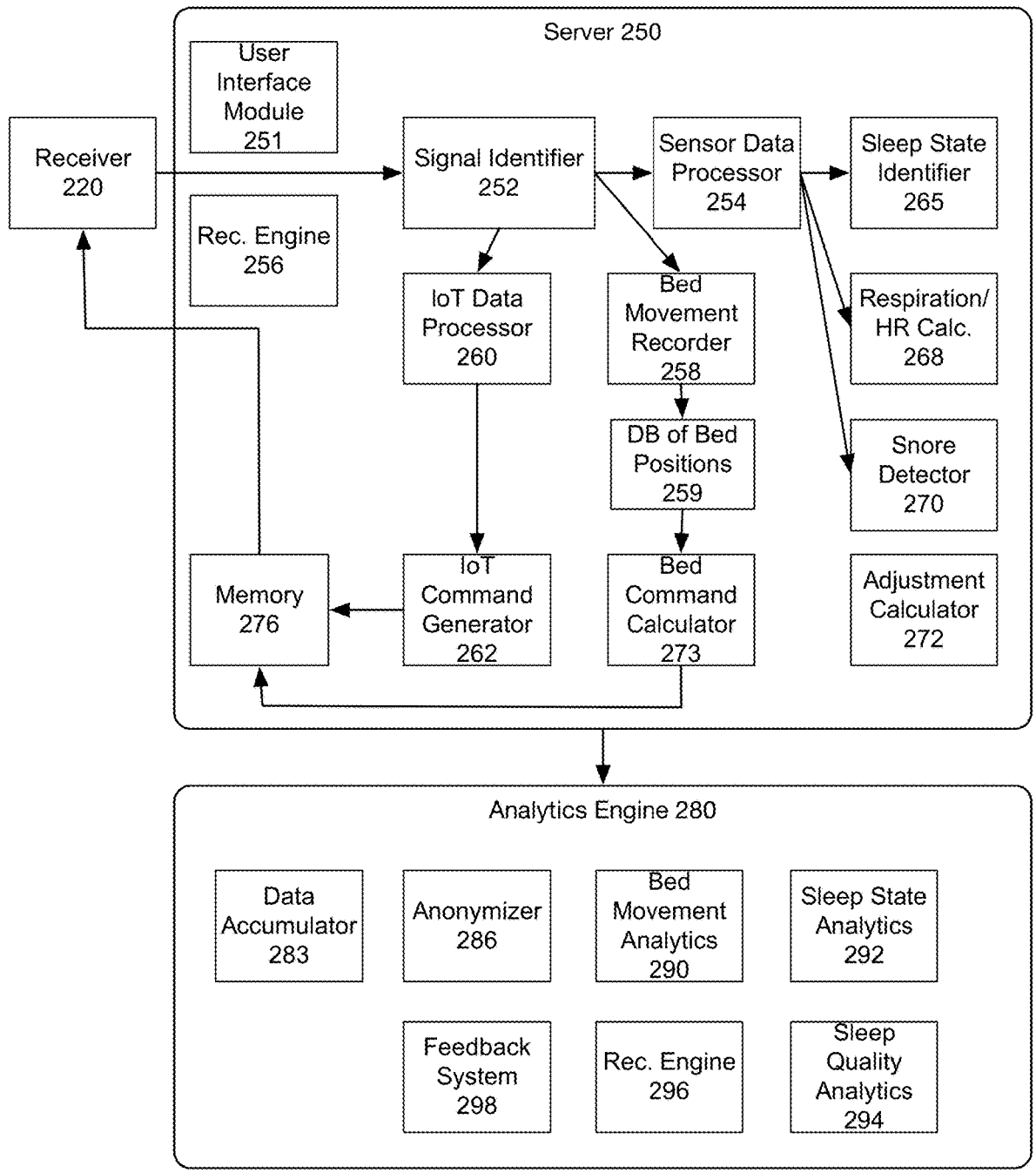
FIG. 2B is a block diagram of one embodiment of the server side portion of the sensor system.

FIG. 2B is a block diagram of one embodiment of the server side portion of the sensor system. The server side portion in one embodiment includes a server 250 and an analytics engine 280. The server 250 processes the user's data, real-time and using a look-back engine, as described in co-pending U.S. patent application Ser. No. 16/601,567, entitled Sleep Detection and Analysis System filed Oct. 14, 2019, now issued as U.S. Pat. No. 11,382,534, and incorporated herein by reference.

Server 250 receives data from receiver 220. The processing utilizes a signal identifier 252 identifies the signal content. The signal in one embodiment may include one or more of: sleep sensor data, environmental sensor data, control data from the bed controller, and IoT data. In one embodiment, the identified signal is sent to the appropriate processor.

The sensor data processor 254 processes the sensor data which is used by sleep state identifier 265 to identify the user's sleep state, and respiration/heartrate calculator 268 to calculate those aspects of the data. In one embodiment, snore detector 270 also uses the sensor data to determine whether the user is snoring or having other respiratory or health issues which may be identified based on the sensor data. In one embodiment, all of the calculated data is stored in memory 276. In one embodiment, the data is stored associated with the environmental sensor data and is stored per user. That is, if there are two sleepers on the bed, in one embodiment, the data is evaluated and stored for each sleeper. In one embodiment, adjustment calculator 272 utilizes the data from sleep state identifier 265, respiration/HR calculator 268, and snore/health detector 270 to determine whether the user's bed and/or environment should be adjusted. If so, adjustment calculator sends an instruction to IoT command generator 262 and/or bed command calculator 273 to make the appropriate adjustment. In one embodiment, if the IoT/bed controls cannot address an identified issue, the user may be alerted through a user interface module 251.

If the data is bed data, bed movement recorder 258 determines what occurred in the bed. In one embodiment, a database of bed position 259 is used in this identification. In one embodiment, the database includes a 'current bed configuration' status, which enables the system to determine an updated bed position. If the bed control data is a request to alter the bed's configuration, the bed command calculator 273 utilizes the command, the current bed configuration, and data about the bed controls to create a command which would correctly move the bed to the requested configuration. This data in one embodiment is stored in memory 276. The updated bed position is also stored in the database 259, and the current bed configuration is updated. In one embodiment, the current bed position is only updated once the receiver has reported the updated position of the bed.

If the signal is an IoT request, the IoT data processor 260 determines what changes should be made, and which IoT device should be instructed. The IoT command generator 262 generates the appropriate commands for the designated IoT device. This data is stored in memory 276 in one embodiment. The IoT command, bed command, or appropriate user feedback is returned to the receiver 220, in one embodiment. Additionally, the server 250 may make the data available to the user via a user interface. The user interface may be presented via a web interface, or an application on the user's system. In one embodiment, the user interface module 251 makes this data available in a format that is comprehensible by the user. In one embodiment, the user interface module 251 provides access to historical data in memory 276 as well as current status data.

Recommendation engine 256 provides recommendations to the user, based on data from analytics engine 280.

Analytics engine 280 utilizes data from a large number of users and calculates sleep state and sleep quality analytics 294 across users. The analytics engine 280 may be used to generate recommendations and feedback to users.

The analytics engine 280 in one embodiment includes a data accumulator 283 which obtains sleep data, environmental data, and user characteristic data. User characteristic data, in one embodiment, is data entered by the user which may impact the user's sleep. For example, user characteristic data may include age, gender, health conditions, use of medications, use of medical devices such as positive airflow devices (CPAPs), etc.

In one embodiment, the data accumulated is anonymized by anonymizer 286. Anonymizer 286 strips identifying data and creates "cumulative" data for analytics. Rather than having data for "Bob, age 55" the system would have data for "users, ages 50-60." This enables the sharing of results derived from this data.

Bed movement analytics 290, sleep state analytics 292, and sleep quality analytics are implemented by a processor and analyze the cumulative data to evaluate the impact of the bed positions, environment, and sleep states on sleep quality. In one embodiment, the analytics engine 280 is attempting to determine recommendations. Recommendations, for example, may be adjustments to the bed configuration, or to the sleep environment, to ensure optimal sleep quality. While recommendation engine 296 utilizes cumulative data from many users' experiences, the server recommendation engine 256 is customized, in one embodiment, to the particular user's personal data. In one embodiment, the recommendations from analytics engine 280 are used for new users (for whom insufficient personal data is available for recommendations) and for users whose situation changes (in which case the prior personal data is no longer relevant). For example, if a user starts utilizing a sleep aid, whether medication or a machine, the recommendation engine 296 may adjust the settings recommended for the user. Other uses of the cumulative data, and personal data, may be made.

In one embodiment, the feedback system 298 of the analytics engine 280 may also be used to provide feedback to a manufacturer of the smart bed. For example, because the receiver obtains bed position and bed movement data, the system can provide information to bed manufacturers regarding ranges of motion, sleep positions, and any real-world issues with the bed.

Figure 3:
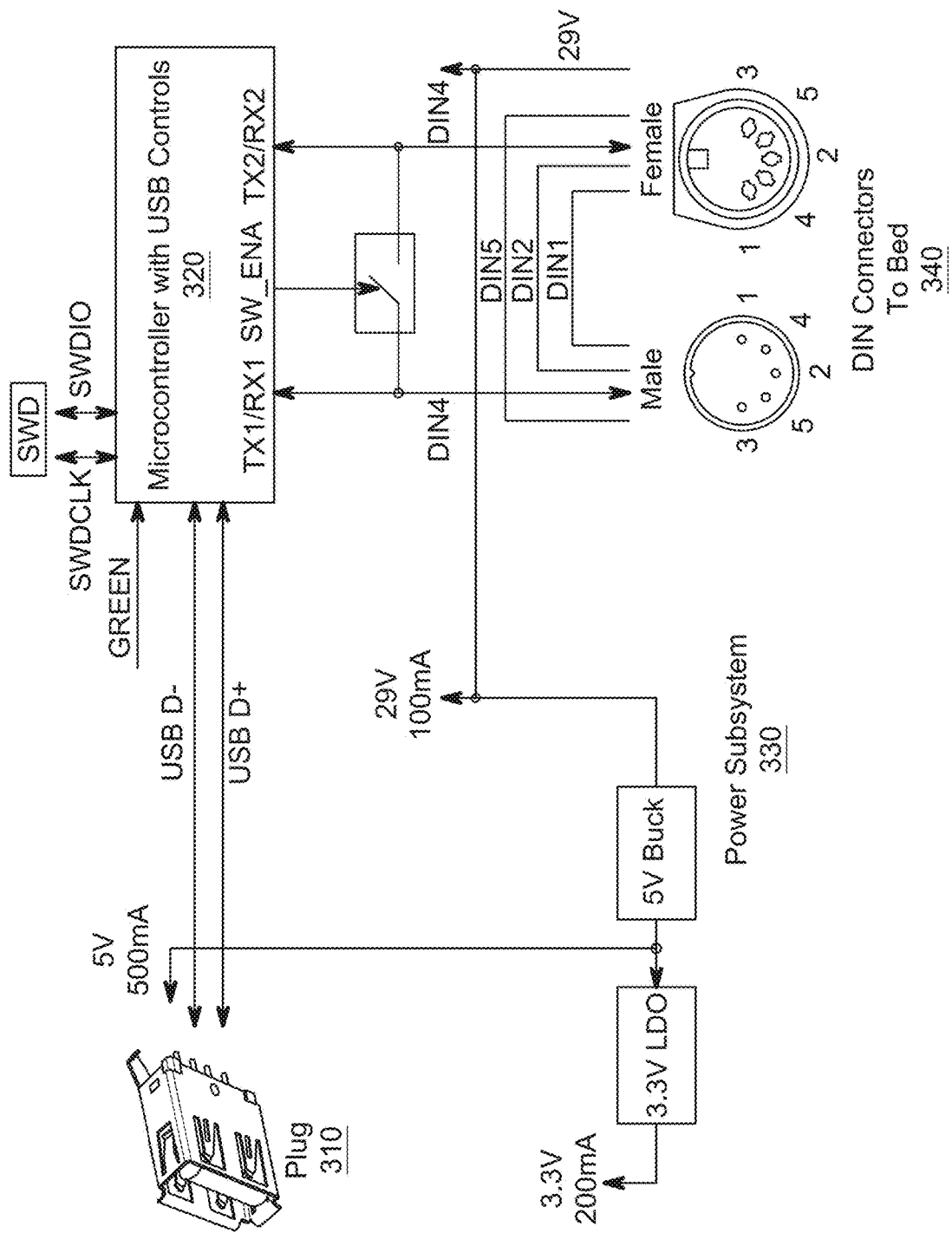
FIG. 3 is a circuit diagram of one embodiment of the connector of the sensor system.

FIG. 3 is a circuit diagram of one embodiment of the connector 222 of the sensor system. In one embodiment, a USB plug 310 provides a USB connection from the connector to the receiver 220. The USB connection goes to microcontroller 320, which is coupled to a connector 340, for connection to the bed. In one embodiment, the connector is a DIN connector 340. In one embodiment, the connector 222 provides a male and female DIN connector, so that the number of DIN connectors available to the bed system remains the same after the connector 222 is plugged in. Of course, while the described embodiment uses a DIN connector 340, an alternative connector mechanism including USB plugs, proprietary plugs, etc. may be used.

The connector 222 also receives power from the DIN connectors 340. The power is coupled through power subsystem 330. In one embodiment, the power subsystem 330 utilizes a low dropout regulator (LDO) and a buck regulator to step down and clean the power signal and provide it via the USB to the receiver 220. In one embodiment, the system provides 3.3 volt DC power to the controller via plug 310.

Figure 4:
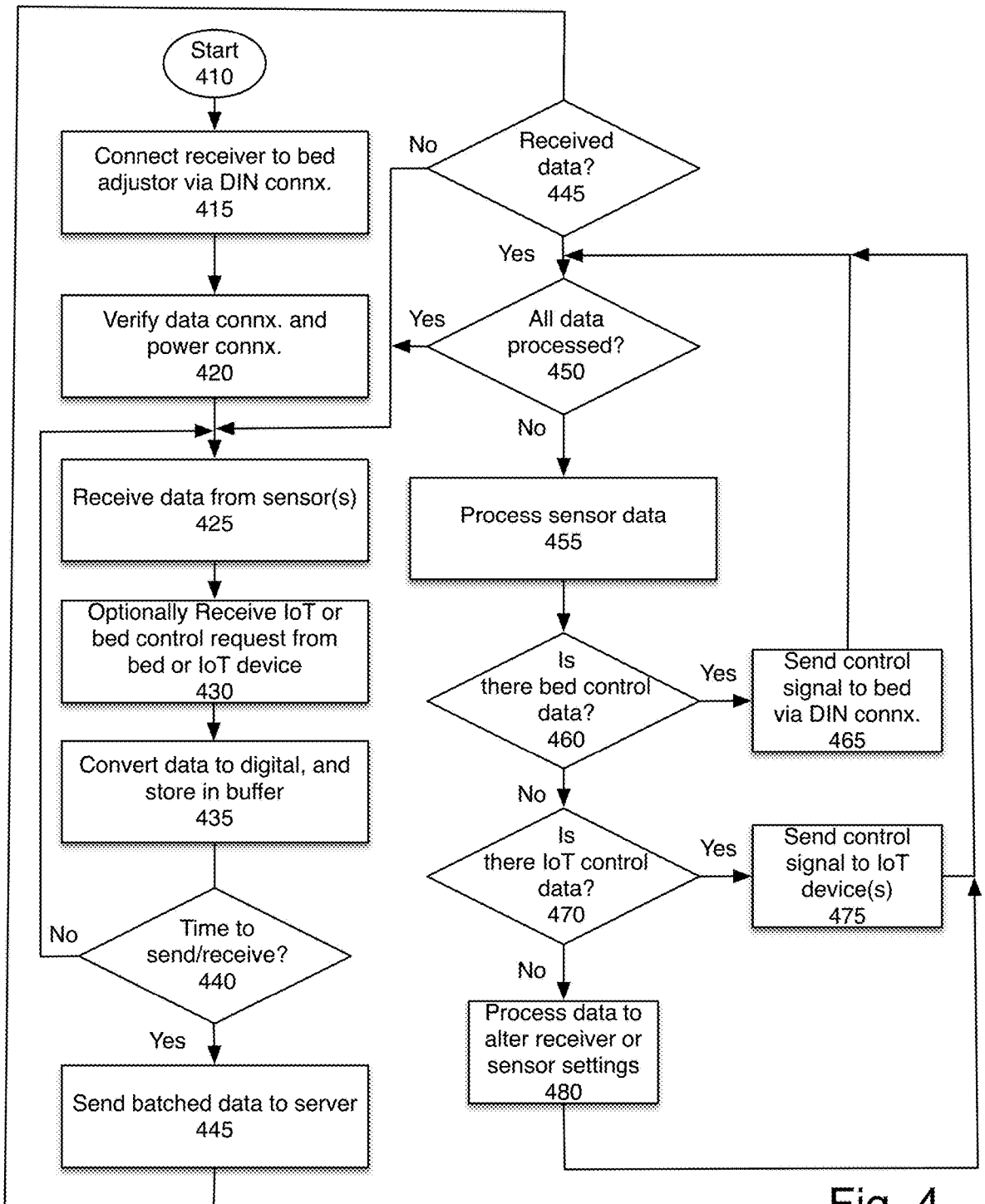
FIG. 4 is an overview flowchart of one embodiment of the sensor system sending and receiving signals.

FIG. 4 is an overview flowchart of one embodiment of the sensor system sending and receiving signals. The process starts at block 410. In one embodiment, this process starts when the user sets up the system initially. In one embodiment, the bed system is set up, and the sensor is correctly positioned under the mattress or within the bed frame.

At block 415, the receiver is connected to the bed, using the DIN connection, in one embodiment.

At block 420, the power and data connection are verified. In one embodiment, the data connection to and from the sensor, and to and from the server is verified. Establishing data connections is well known in the art. In one embodiment, if the receiver uses a wireless connection, the user may identify the wireless network, and password to establish the data connection.

At block 425, data from the sensor is received.

At block 430, an IoT or bed control request is received, in one embodiment. The request may be from the bed or a separate IoT device. The request in one embodiment may be a request to change a configuration of the bed or the environment.

At block 435, the data received from the sensors and control request data when received, is converted to digital format. In one embodiment, the data is encoded for transmission. In one embodiment, a lossless encoding method is used. In one embodiment, the data is temporarily stored in a memory, such as a buffer.

At block 440 the process determines if it is time to send/receive data, in one embodiment. In one embodiment, data is sent at regular intervals in batches. In another embodiment, data is sent continuously. If it is not yet time to send data, the process returns to block 425 to continue receiving sensor data.

If it is time to send the data, the process sends batched data to the server. The data includes buffered sensor data and when an IoT request is received, IoT data, in one embodiment. At block 445, the process determines whether data was received at the server. If no data was received, which means that there was no sensor data or IoT data sent, the process returns to block 425, to continue awaiting data from sensors and/or IoT devices.

If data was received, the system at block 450 determines whether the data has been processed. If so, the system returns to awaiting data.

At block 455, the sensor data is processed. In one embodiment, this includes determining the user's current sleep state, and any other relevant data about the user. In one embodiment, sleep sensor data is also supplemented with other sensor data. In one embodiment, this processed sensor data is stored. In one embodiment, the system also determines whether, based on the analysis of the sleep sensor data and other sensor data, the user's environments should be altered. If so, in one embodiment, the process may generate IoT/bed control data. The process then continues to block 460.

At block 460 the system determines whether there is bed control data. If so, at block 465, the system prepares a control signal to be sent to the bed, via the DIN connection. In one embodiment, the control signal is translated into a format that the bed controller can receive. In one embodiment, if the command is relative absolute (e.g. raise the head of the bed to a 10 degree angle) the system further translates that command to an adjustment based on data from the known current position of the bed (e.g. move the angle of the bed by 4 degrees up.) The control signal is translated into a format which is usable by the bed controller. For example, the translation may be as follows:

receive command: raise the head of the bed to a 10 degree angle determine current position of bed: head raised to a 6 degree angle translate command to change command: raise head by 4 degrees translate command to bed controller command: turn on motor #2 for 30 seconds.

The process then returns to block 450, to determine whether all data has been processed.

If there is no bed control data, as determined at block 460, the process determines whether there is IoT control data, at block 470. IoT control data is used to adjust elements in the user's environment. This may include elements that directly impact the sleep, such as turning on or off lights, fans, noise machines, etc. as well as other elements like locking doors, closing garage doors, turning on coffee machines, etc. If the data is IoT control data, ta block 475 control signals are sent to the appropriate IoT device. In one embodiment, the control signals are sent through the bed's system, as described above.

If the data is neither bed control data nor IoT data, it is processed to alter receiver or sensor settings. The resultant data is sent to the receiver, if appropriate. This process runs when the system is active.

Figure 5:
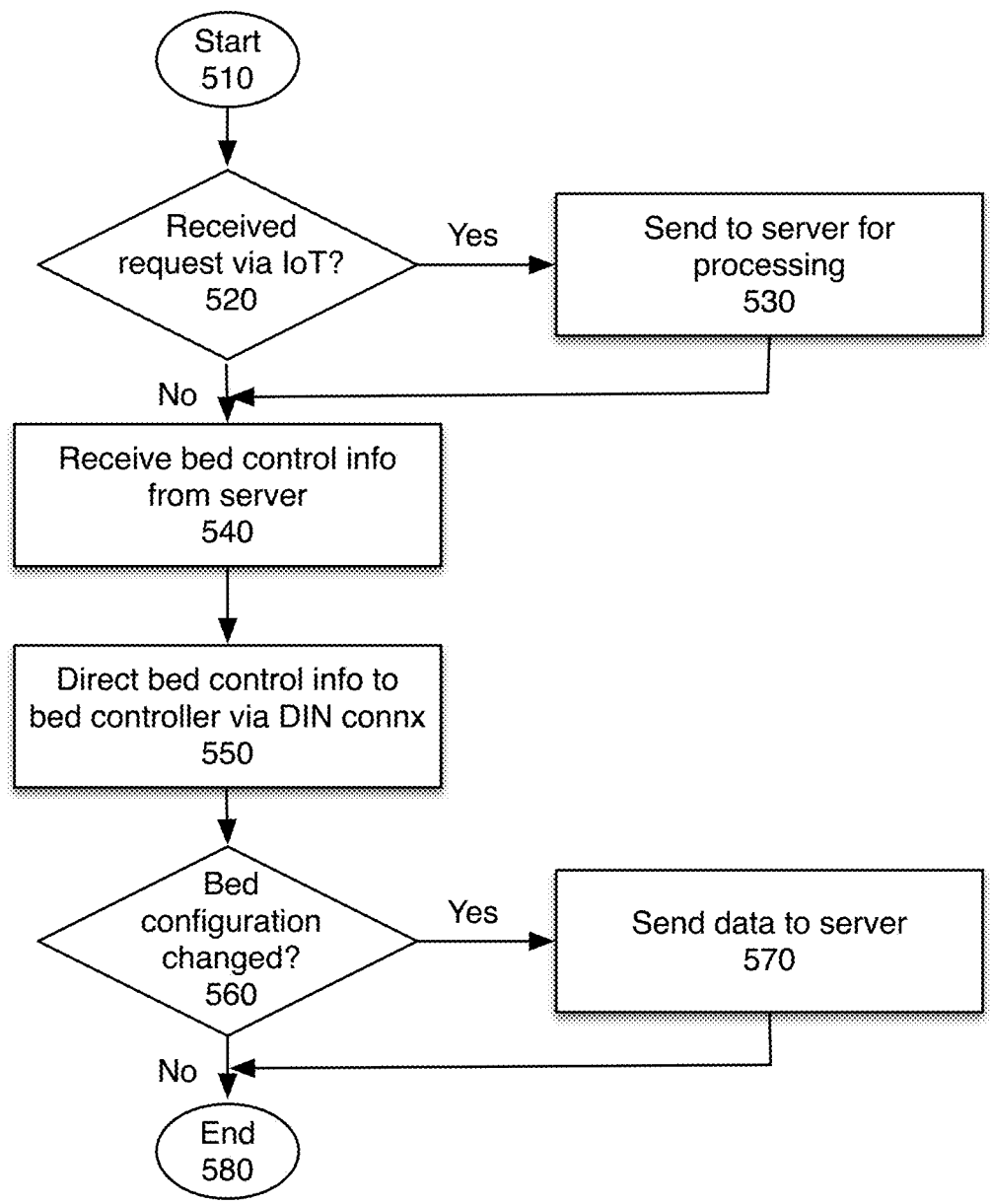
FIG. 5 is a flowchart of one embodiment of controlling the bed via the signals from the receiver.

FIG. 5 is a flowchart of one embodiment of controlling the bed via the signals from the receiver. The process starts at block 510. In one embodiment, the process starts when a bed adjustment request is received. At block 520 the process determines whether the request was received via an Internet of Things interface. If so, at block 530 the request is sent to the server for processing.

At block 540, bed control information is received from the server. In one embodiment, the bed control information is customized for the particular smart bed associated with the user's account and in a format which the bed can utilize. In one embodiment, the server translates control data to this format, prior to sending it to the receiver.

At block 550, the bed control information is directed to the bed controller. In one embodiment, this is done via a DIN connection cable.

At block 560, the process determines whether the bed configuration was changed. If so, the data is sent to the server 570. This is used to confirm bed configuration changes, and also track current and past bed configurations. In one embodiment, the verification occurs because the command may result in no change, either because the bed is already in that configuration, or because the bed cannot achieve the requested configuration. In one embodiment, when the server receives a configuration request, it determines whether the bed is already in that configuration and alerts the user. In one embodiment, the server does not send a configuration command if that is the case. The process ends at block 580.

Figure 6:
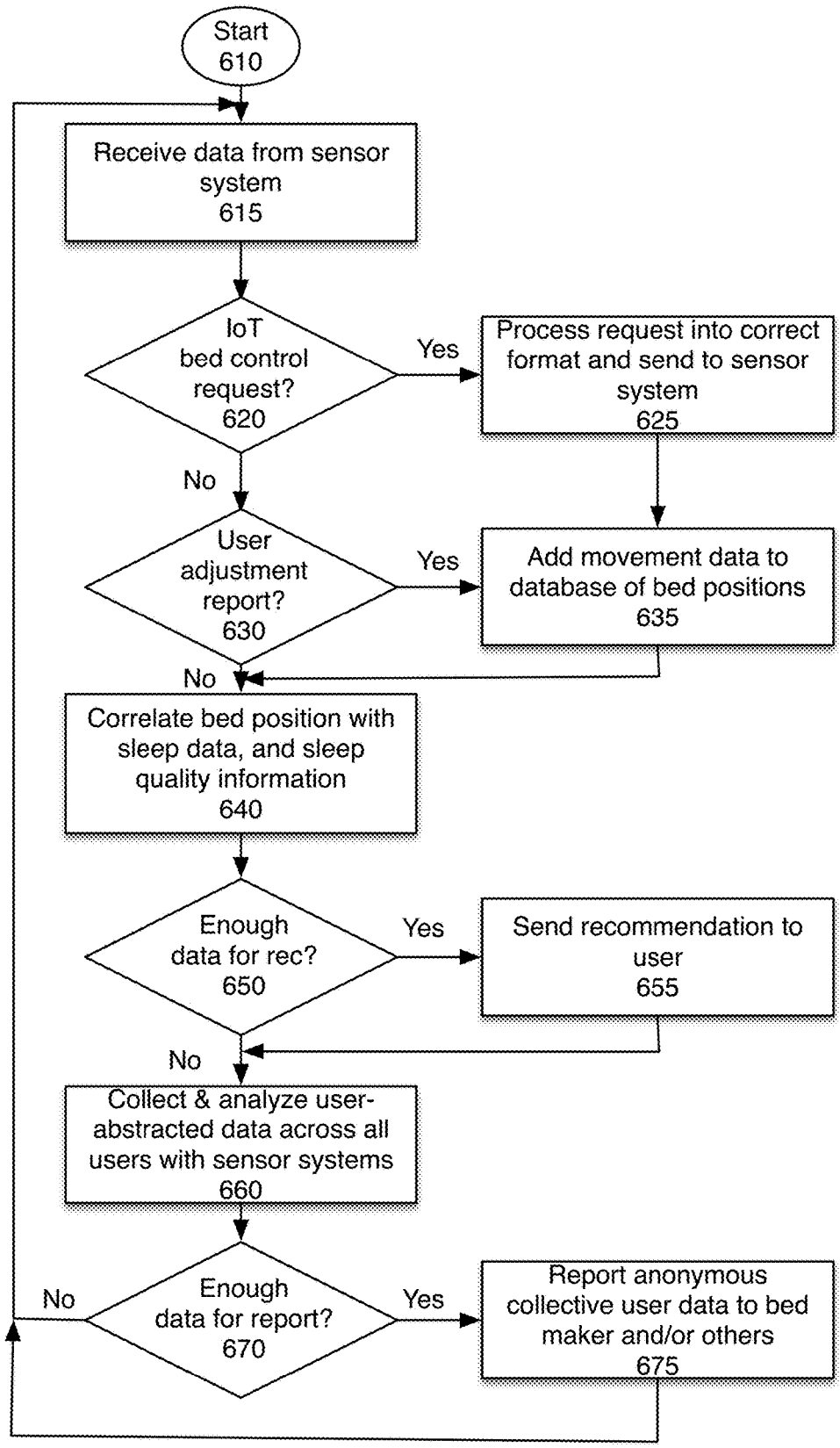
FIG. 6 is a flowchart of one embodiment of providing feedback regarding bed movement.

FIG. 6 is a flowchart of one embodiment of providing feedback regarding bed movement. The process starts at block 610. At block 615, data is received from the sensor system. This data is movement data, and as discussed above is used by the server to determine the user's sleep state, and in one embodiment optimize the user's sleep environment.

At block 620, the process determines whether an IoT bed control request has been received. An IoT bed control request is a request from the user, utilizing an IoT device such as APPLE's Siri or GOOGLE's Home device, requesting an adjustment in the position or configuration of the bed. In one embodiment, the bed may have adjustable positions for the head and foot of the bed. In one embodiment, the bed may also have adjustable heating/cooling, airflow, and/or other aspects. If an IoT bed control request is received, at block 625 the request is processed into a command which can be transmitted to the bed via the receiver, and sent to the receiver. The processing, which includes interpretation and analysis, occurs on the server side, in one embodiment. In one embodiment, the IoT device receives "natural language" commands verbally, which are initially analyzed by the IoT device, and then passed to the server. The commands generally are relative commands (e.g. raise the head of the bed), which are interpreted by the server based on the known current position data.

The process then continues to block 635. In one embodiment, at block 635, the movement data is added to the database of bed positions. The process then continues to block 640.

If the data did not include an IoT bed control request, the process at block 630 determines whether the data include a user adjustment report. A user adjustment report provides data about manual adjustments made directly by the user, using a remote control or another method of controlling the bed configuration. If the data includes a user adjustment report, at block 635, the movement data is added to the database of bed positions 635. In one embodiment, the movement data (e.g. head moved up by 10 degrees) is added to the existing position data, to determine a "current position." In one embodiment, the database of bed positions includes a "current position" which is used as the basis for the next bed adjustment, whether automatic or via control requests. The database in one embodiment also includes historical movement data and position data.

At block 640, the bed position is correlated with sleep data and sleep quality information. This data may be used in analyzing the impact of bed configuration on sleep quality. The results of such analysis may be used to provide recommendations to the user and/or automatic adjustments if the user authorizes such adjustments.

At block 650, the process determines whether there is enough data for a recommendation regarding bed configuration. If so, the recommendation is sent to the user at block 655. In one embodiment, the user may authorize the implementation of such recommendations. If that is the case, the system may automatically made adjustments based on the analysis. In one embodiment, at the time of set-up the user may authorize the system to automatically adjust the bed to improve sleep quality.

At block 680 the user abstracted data, that is anonymized data, is collected from multiple users. At block 670 the data is analyzed and the process determines whether there is enough data for reporting. If so, at block 675, the system reports the data. In one embodiment, the reporting may be to the bed manufacturer. In one embodiment, the report may be to users, as global recommendations or analysis data. This information may be useful for creating recommendations for users and for manufacturers. It may also be useful for adjusting recommendation based on user conditions. For example, the system may determine based on analysis of cumulative data that teenagers sleep better with their feet elevated, compared to adults or children, or that someone with a health condition sleeps better with a particular bed and/or environmental adjustment. The process then returns to block 615 to continue receiving data.

Of course, though FIGS. 4 through 6 are shown as a flowcharts, in one embodiment they may be implemented as interrupt-driven systems and the ordering of individual elements may be altered unless they are dependent on each other. For example, in FIG. 6, the reports, requests, and recommendations may be independently obtained and the appropriate analysis may be triggered whenever relevant data is received.

Figure 7:
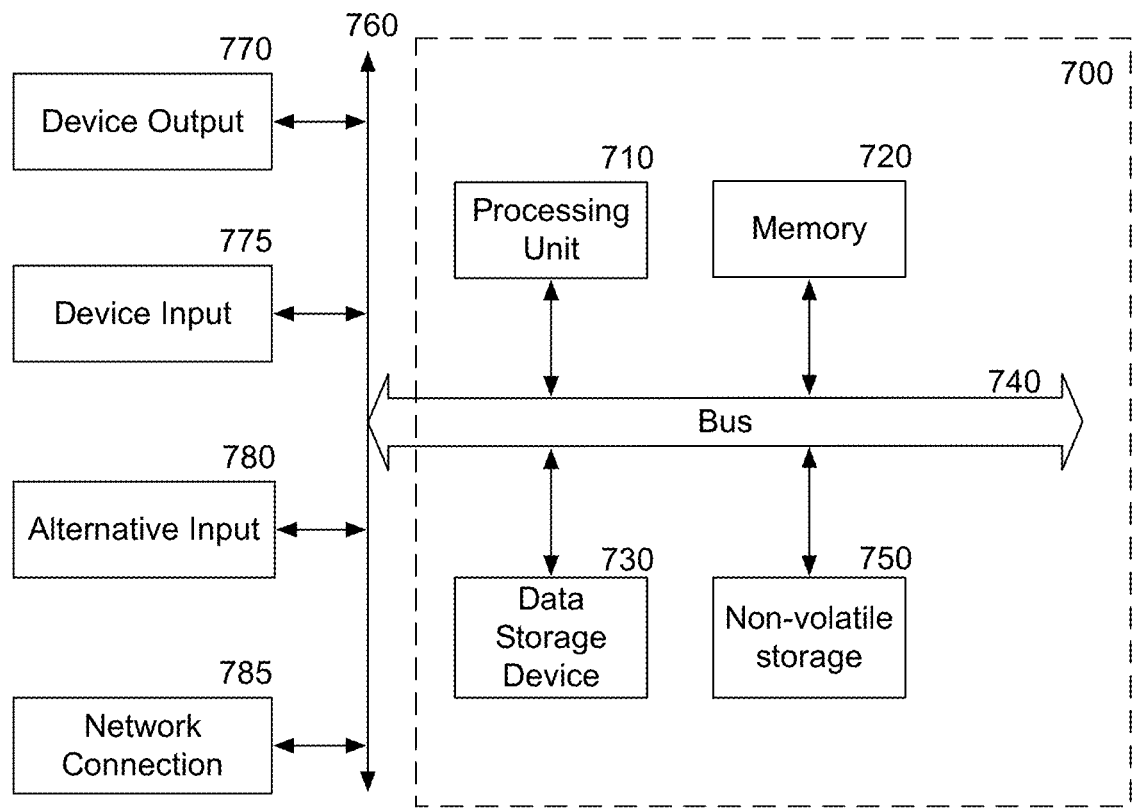
FIG. 7 is a block diagram of one embodiment of a computer system that may be used as the sensor

FIG. 7 is a block diagram of one embodiment of a computer system that may be used with the present invention. It will be apparent to those of ordinary skill in the art, however that other alternative systems of various system architectures may also be used. Furthermore, while this is a particular computer system, the processors, servers, and other computer devices described may be implemented in a distributed cloud-based environment in which portions of a computer system's capabilities are used to provide the described features and processes.

The data processing system illustrated in FIG. 7 includes a bus or other internal communication means 740 for communicating information, and a processing unit 710 coupled to the bus 740 for processing information. The processing unit 710 may be a central processing unit (CPU), a digital signal processor (DSP), or another type of processing unit 710.

The system further includes, in one embodiment, a random access memory (RAM) or other volatile storage device 720 (referred to as memory), coupled to bus 740 for storing information and instructions to be executed by processor 710. Main memory 720 may also be used for storing temporary variables or other intermediate information during execution of instructions by processing unit 710.

The system also comprises in one embodiment a read only memory (ROM) 750 and/or static storage device 750 coupled to bus 740 for storing static information and instructions for processor 710. In one embodiment, the system also includes a data storage device 730 such as a magnetic disk or optical disk and its corresponding disk drive, or Flash memory or other storage which is capable of storing data when no power is supplied to the system. Data storage device 730 in one embodiment is coupled to bus 740 for storing information and instructions.

The system may further be coupled to an output device 770, such as a cathode ray tube (CRT) or a liquid crystal display (LCD) coupled to bus 740 through bus 760 for outputting information. The output device 770 may be a visual output device, an audio output device, and/or tactile output device (e.g. vibrations, etc.)

An input device 775 may be coupled to the bus 760. The input device 775 may be an alphanumeric input device, such as a keyboard including alphanumeric and other keys, for enabling a user to communicate information and command selections to processing unit 710. An additional user input device 780 may further be included. One such user input device 780 is cursor control device 780, such as a mouse, a trackball, stylus, cursor direction keys, or touch screen, may be coupled to bus 740 through bus 760 for communicating direction information and command selections to processing unit 710, and for controlling movement on display device 770.

Another device, which may optionally be coupled to computer system 700, is a network device 785 for accessing other nodes of a distributed system via a network. The communication device 785 may include any of a number of commercially available networking peripheral devices such as those used for coupling to an Ethernet, token ring, Internet, or wide area network, personal area network, wireless network or other method of accessing other devices. The communication device 785 may further be a null-modem connection, or any other mechanism that provides connectivity between the computer system 700 and the outside world.

Note that any or all of the components of this system illustrated in FIG. 7 and associated hardware may be used in various embodiments of the present invention.

It will be appreciated by those of ordinary skill in the art that the particular machine that embodies the present invention may be configured in various ways according to the particular implementation. The control logic or software implementing the present invention can be stored in main memory 720, mass storage device 730, or other storage medium locally or remotely accessible to processor 710.

It will be apparent to those of ordinary skill in the art that the system, method, and process described herein can be implemented as software stored in main memory 720 or read only memory 750 and executed by processor 710. This control logic or software may also be resident on an article of manufacture comprising a computer readable medium having computer readable program code embodied therein and being readable by the mass storage device 730 and for causing the processor 710 to operate in accordance with the methods and teachings herein.

The present invention may also be embodied in a handheld or portable device containing a subset of the computer hardware components described above. For example, the handheld device may be configured to contain only the bus 740, the processor 710, and memory 750 and/or 720.

The handheld device may be configured to include a set of buttons or input signaling components with which a user may select from a set of available options. These could be considered input device #1 775 or input device #2 780. The handheld device may also be configured to include an output device 770 such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above, such as a server system. For example, the appliance may include a processing unit 710, a data storage device 730, a bus 740, and memory 720, and no input/output mechanisms, or only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism. In one embodiment, the device may not provide any direct input/output signals, but may be configured and accessed through a website or other network-based connection through network device 785.

It will be appreciated by those of ordinary skill in the art that any configuration of the particular machine implemented as the computer system may be used according to the particular implementation. The control logic or software implementing the present invention can be stored on any machine-readable medium locally or remotely accessible to processor 710. A machine-readable medium includes any mechanism for storing information in a form readable by a machine (e.g. a computer). For example, a machine readable medium includes read-only memory (ROM), random access memory (RAM), magnetic disk storage media, optical storage media, flash memory devices, or other storage media which may be used for temporary or permanent data storage. In one embodiment, the control logic may be implemented as transmittable data, such as electrical, optical, acoustical or other forms of propagated signals (e.g. carrier waves, infrared signals, digital signals, etc.).

In the foregoing specification, the invention has been described with reference to specific exemplary embodiments thereof. It will, however, be evident that various modifications and changes may be made hereto without departing from the broader spirit and scope of the invention as set forth in the appended claims. The specification and drawings are, accordingly, to be regarded in an illustrative rather than a restrictive sense.

We claim:

1. A sleep sensor system comprising:
 a sensor to collect movement data from a sleeper on an adjustable bed;
 a receiver to send movement data from the sensor to a server and to receive command data from the server, the command data comprising instructions to alter a configuration of the adjustable bed, the command data received from a bed command calculator of the server, the bed command calculator configured to calculate the command data to control the adjustable bed, based on a combination of a current position of the bed, the movement data, and a requested update to a configuration of the bed;
 a bed controller to receive the command data from the receiver and to transmit bed movement instructions to the adjustable bed, to cause the adjustable bed to alter one or more of its settings in response to the bed movement instructions.

2. The sleep sensor system of claim 1, further comprising:
 a connector to interface between a bed adjustor associated with the adjustable bed, and the receiver.

3. The sleep sensor system of claim 2, wherein the connector includes the bed controller.

4. The sleep sensor system of claim 2, wherein the connector provides power to the receiver.

5. The sleep sensor system of claim 4, wherein the connector receives power from a bed adjustor, incorporated into the adjustable bed.

6. The sleep sensor system of claim 4, wherein the power from the connector is stepped down by a power system in the receiver.

7. The sleep sensor system of claim 1, further comprising:
 an Internet of Things (IoT) controller to transmit IoT command data received from the server to an IoT device to cause the IoT device to take an action, the IoT controller is further to receive instructions from an IoT device to control the adjustable bed; and
 the receiver further to receive the command data from the server to make an adjustment, based on the instructions from the IoT device.

8. The sleep sensor system of claim 7, wherein the bed movement command data is customized to the adjustable bed.

9. The sleep sensor system of claim 7, wherein the IoT controller is used to adjust a sleeping environment of a user.

10. The sleep sensor system of claim 1, further comprising:
 a server to receive the movement data from the receiver, the server to analyze the movement data from the sensor, and to send control signals to control the adjustable bed to the receiver.

11. A method of controlling a sleep environment including an adjustable bed comprising:
 sensing movement data using a sensor in the adjustable bed;
 collecting the movement data at a receiver;
 collecting environmental sensor data, monitoring a sleep environment, at the receiver;

sending the movement data to a server;
receiving command data from the server, the command data to adjust the adjustable bed, wherein the command data is received from a bed command calculator in the server, the bed command calculator configured to calculate the command data to control the adjustable bed, based on a combination of a current position of the bed and a requested update to a bed configuration;
transmitting, using a bed controller, bed movement command data to the adjustable bed, the bed movement command data based on the received command data, causing the adjustable bed to alter one or more of its settings.

12. The method of claim 11, further comprising:
coupling the receiver to the adjustable bed via a connector to interface between a bed adjustor and the receiver.

13. The method of claim 12, wherein the connector includes the bed controller.

14. The method of claim 12, wherein the connector provides power to the receiver.

15. The method of claim 14, wherein the connector receives power from a bed adjustor, incorporated into the adjustable bed.

16. The method of claim 14, further comprising:
stepping down the power from the connector by a power system in the receiver.

17. The method of claim 11, further comprising:
receiving a voice instruction to alter the adjustable bed settings via an IoT device; and
generating the command data to adjust the bed based on the voice instruction.

18. The method of claim 11, further comprising:
analyzing the movement data to identify a sleep state, respiration, heart rate, snoring;
determining whether a change should be made to the adjustable bed or the sleep environment should be made based on the analyzing; and
when the change is identified, generating a command to make the change.

19. A system to retrofit an adjustable bed, the system comprising:
a sensor to obtain sleep data, for placement in the bed;
a connector to couple to controls for the adjustable bed;
a receiver to interface with the adjustable bed through the connector, the receiver comprising:
a signal receiver to receive sleep data from the sensor;
a digitizer to convert sensor data to digital data;
a transceiver to send the digital data to a server, and to receive command data from the server;
a server comprising:
a bed command calculator to calculate a command to control the adjustable bed, based on a combination of a current position of the bed and a requested update to a bed configuration, the command sent to the receiver, and used by the receiver to trigger a bed adjustor in the adjustable bed.

20. The system of claim 19, further comprising:
a server further comprising:
a signal identifier to identify the requested update to a bed configuration, based on one of: an instruction received from an IoT device, a manual change made by a user, and a change to be made based on analysis of the digital data.

* * * * *